(12) United States Patent
Huang et al.

(10) Patent No.: US 9,707,048 B2
(45) Date of Patent: Jul. 18, 2017

(54) MEDICAL PENDANT HAVING AN ELECTRIC INTERFACE

(71) Applicant: MAQUET (SUZHOU) CO., LTD., Suzhou (CN)

(72) Inventors: Jiasheng Huang, Suzhou (CN); Wei Zhang, Suzhou (CN); Qunhua Li, Suzhou (CN); Ming Ji, Suzhou (CN)

(73) Assignee: MAQUET (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 15/287,035

(22) Filed: Oct. 6, 2016

(65) Prior Publication Data

US 2017/0035524 A1     Feb. 9, 2017

Related U.S. Application Data

(63) Continuation of application No. PCT/CN2014/083513, filed on Aug. 1, 2014.

(30) Foreign Application Priority Data

Apr. 30, 2014 (CN) .......................... 2014 1 0181261

(51) Int. Cl.
*H01R 25/00* (2006.01)
*A61B 90/00* (2016.01)
*A61G 12/00* (2006.01)
*H01R 25/14* (2006.01)

(52) U.S. Cl.
CPC .............. *A61B 90/08* (2016.02); *A61B 90/00* (2016.02); *A61G 12/002* (2013.01); *H01R 25/14* (2013.01)

(58) Field of Classification Search
CPC ........ H01R 25/14; A61B 90/08; A61G 12/002

USPC .......... 439/116, 110, 120, 121, 122; 280/35
See application file for complete search history.

(56) References Cited

U.S. PATENT DOCUMENTS

| 4,243,284 | A | * | 1/1981 | Humphreys | ........... H01R 25/14 |
|---|---|---|---|---|---|
| | | | | | 439/113 |
| 4,776,809 | A | * | 10/1988 | Hall | ...................... H01R 25/142 |
| | | | | | 248/222.52 |
| 5,348,485 | A | * | 9/1994 | Briechle | ................ H01R 25/14 |
| | | | | | 439/110 |
| 7,258,555 | B2 | * | 8/2007 | Tiesler | ................... H01R 25/14 |
| | | | | | 439/110 |

(Continued)

FOREIGN PATENT DOCUMENTS

| CN | 1036932 A | 11/1989 |
|---|---|---|
| CN | 2195801 Y | 4/1995 |

(Continued)

OTHER PUBLICATIONS

English translation of International Search Report dated Jan. 28, 2015, issued for corresponding International Application No. PCT/CN2014/083513, 2 pages.

*Primary Examiner* — Abdullah Riyami
*Assistant Examiner* — Nader Alhawamdeh

(57) ABSTRACT

A medical pendant is disclosed. The medical pendant has a medical pendant post that extends along a longitudinal direction of the medical pendant, the medical pendant post including an electric interface. The electric interface includes a groove disposed in the medical pendant post and extending along the longitudinal direction of the medical pendant post, an insulator disposed in the groove, and a conductor disposed within the insulator.

20 Claims, 4 Drawing Sheets

(56) References Cited

U.S. PATENT DOCUMENTS

| | | | |
|---|---|---|---|
| 7,845,601 B1 * | 12/2010 | Culpepper | A61G 7/05 248/125.2 |
| 7,914,198 B2 * | 3/2011 | Mier-Langner | F21S 8/038 361/674 |
| 8,770,993 B2 * | 7/2014 | Gingrich, III | H01R 25/142 439/121 |
| 8,992,238 B2 * | 3/2015 | Chinn | F16B 21/09 439/116 |
| 2005/0152132 A1 * | 7/2005 | Bernhart | F21S 8/06 362/147 |
| 2009/0201632 A1 | 8/2009 | Bauer et al. | |
| 2010/0211001 A1 | 8/2010 | Kawata | |
| 2011/0070755 A1 * | 3/2011 | Boecker | H01R 9/2691 439/121 |
| 2013/0143423 A1 * | 6/2013 | Luksic | H01R 25/142 439/116 |
| 2013/0307237 A1 * | 11/2013 | Chen | A61G 12/001 280/35 |
| 2013/0335983 A1 * | 12/2013 | Nicieja | F21V 21/35 362/382 |
| 2014/0227892 A1 * | 8/2014 | Chinn | F16B 21/09 439/116 |

FOREIGN PATENT DOCUMENTS

| | | | |
|---|---|---|---|
| CN | 2726156 Y | | 9/2005 |
| CN | 101889932 A | | 11/2010 |
| CN | 101940499 A | | 1/2011 |
| CN | 201710467 U | * | 1/2011 |
| CN | 201798873 U | | 4/2011 |
| CN | 102058461 A | | 5/2011 |
| CN | 201920915 U | | 8/2011 |
| CN | 202096297 U | | 1/2012 |
| CN | 202236081 U | | 5/2012 |
| CN | 103142312 A | | 6/2013 |
| CN | 203153956 U | | 8/2013 |
| CN | 103591425 A | | 2/2014 |
| CN | 101889899 B | | 7/2014 |
| CN | 103919615 A | | 7/2014 |
| CN | 104055576 A | | 9/2014 |
| CN | 203815593 U | | 9/2014 |
| EP | 0603093 A1 | | 6/1994 |
| EP | 2058911 B1 | | 12/2009 |

* cited by examiner

MEDICAL PENDANT HAVING AN ELECTRIC INTERFACE

CROSS REFERENCE TO RELATED APPLICATIONS

The present application is a continuation-in-part filed under 35 U.S.C. §111(a), and claims the benefit under 35 U.S.C. §§365(c) and 371 of PCT International Application No. PCT/CN2014/083513, filed Aug. 1, 2014, and which designates the United States of America, and Chinese Patent Application No. 201410181261.8, filed Apr. 30, 2014. The disclosures of these applications are herein incorporated by reference in their entirety.

TECHNICAL FIELD

The present invention relates to the technical field of medical equipment, and more particularly to a medical pendant box body and posts used for the medical pendant box body.

BACKGROUND

Medical pendants are a type of medical equipment used in modern hospital operating rooms, intensive care units and the like, and various accessories such as handle, laminate and the like are often fixed (e.g., installed) to the medical pendant so as to achieve various functions. The main structure of a medical pendant is a box body. Therefore, in order to achieve the mechanical connection and electrical connection to various medical accessories, various mechanical interfaces and electrical interfaces are typically set on the medical pendant box body.

Since the structure and/or the appearance of conventional medical pendant box bodies vary, the modes for the interfaces thereof are also different from each other, and switch connection blocks are installed if various interfaces are to be interchanged. Also, connecting electrical cables for conventional medical pendant boxes can involve large time consumption. Further, a position of a conventional medical accessory is fixed and the height and/or position thereof cannot be freely adjusted.

SUMMARY OF THE DISCLOSURE

In at least some exemplary embodiments, the present medical pendant box body can have standardised interfaces, without involved arrangements of connecting electrical cables, and therefore being simplified for disassembly and assembly and the position of a medical accessory being capable of being freely adjusted.

In at least some exemplary embodiments, the medical pendant box body may comprise at least two panels, at least two posts extending along the longitudinal direction of the medical pendant box body, an upper base plate and a lower base plate, the at least two panels being respectively fixed to the at least two posts, the upper base plate and the lower base plate being respectively fixed to the upper edge and the lower edge of each panel of the at least two panels, at least one post of the at least two posts being provided with an electrical interface, the electrical interface comprising an inner groove located on the post and extending along the longitudinal direction of the post, an insulator accommodated within the inner groove, and a conductor sealed within the insulator.

In at least some exemplary embodiments, the medical pendant box body of the present invention can have the following features: a standardised interface can be provided, electrical cables may not be connected in a complicated manner, and disassembly may be simplified and the position of a medical accessory can be freely adjusted.

In at least some exemplary embodiments, the inner groove may be substantially filled when the insulator is accommodated within the inner groove and the conductor is sealed within the insulator.

In at least some exemplary embodiments, the medical pendant box body can have the following features: the electrical interface may have suitable reliability and insulation performance, substantially preventing the infiltration of water or other cleaning agents during the cleaning process in a hospital.

In at least some exemplary embodiments, the number of the insulators within the inner groove may be two, and one conductor may be sealed within each insulator.

In at least some exemplary embodiments, the medical pendant box body can have the following features: by the appropriate number and settings of the above insulators and conductors, a simple and reliable connection between the plug of the electrical accessory and the conductor inside the post can be achieved.

In at least some exemplary embodiments, the cross section of the conductors may be substantially Y-shaped or Ω-shaped.

In at least some exemplary embodiments, the medical pendant box body can have the following features: by the appropriate shape of the above conductors, a simple and reliable connection between the plug of the electrical accessory and the conductor inside the post can be achieved.

In at least some exemplary embodiments, the insulator may comprise an insulator front part and an insulator rear part, the conductor being sealed within the insulator rear part, the insulator front part having a substantially flat front surface and a gap extending along the longitudinal direction of the medical pendant box body.

In at least some exemplary embodiments, the medical pendant box body can have the following features: the gap can be provided for inserting the plug of the electrical accessory, which may facilitate the simple and reliable connection between the plug of the electrical accessory and the conductor inside the post.

In at least some exemplary embodiments, the width size of the gap and the elasticity of the insulator front part may be designed so that the gap can be provided for inserting the plug of an electrical accessory and the insulator front part being substantially sealed before inserting the plug.

In at least some exemplary embodiments, the medical pendant box body can have the following features: the simple and reliable connection between the plug of the electrical accessory and the conductor inside the post is achieved, meanwhile susbstantially preventing the infiltration of water or other cleaning agents during the cleaning process in a hospital.

In at least some exemplary embodiments, the width size of the inner groove and the elasticity of the insulator may be designed to make the insulator produce suitable predeformation so as to produce certain pre-pressure, so that when the plug of an electrical accessory is inserted into the electrical interface to connect to the conductor, the pre-pressure may substantially prevent the plug from disengaging from the conductor.

According to the exemplary embodiments described above, the medical pendant box body can have the following features: the reliability of the connection between the plug of the electrical accessory and the conductor may be suitable, and the disengagement of the plug from the conductor may be substantially prevented.

In at least some exemplary embodiments, the conductor may be connected to the control board of the medical pendant via a connector.

According to the exemplary embodiments described above, the medical pendant box body can have the following features: multiple functions such as air brake control, electromagnetic brake control, motor control, direct current supply, video or audio signal supply and the like can be accomplished by the control board.

In at least some exemplary embodiments, at least one post of the at least two posts may be provided with a mechanical interface, the mechanical interface comprising a concave curved portion or a convex curved portion for matching to the convex curved portion or the concave curved portion of a mechanical connecting piece.

In at least some exemplary embodiments, the medical pendant box body can have the following features: by the same post in the medical pendant box body, both the mechanical connection and the electrical connection can be achieved, the number of the components involved may be reduced, and the connection reliability may be suitable; furthermore, a medical accessory may be easy to be disassembled and assembled, and the position of the medical accessory can be freely and steplessly adjusted.

In at least some exemplary embodiments, the mechanical connecting piece may be used for installing a medical accessory.

In at least some exemplary embodiments, the medical pendant box body can have the following features: the medical accessory can be freely adjusted with respect to its height and/or position and can be simply and reliably installed to the medical pendant box body.

In at least some exemplary embodiments, a post used for the medical pendant may extend along the longitudinal direction of the medical pendant box body, the post being provided with an electrical interface, the electrical interface comprising an inner groove located on the post and extending along the longitudinal direction of the post, an insulator accommodated within the inner groove, and a conductor sealed within the insulator.

In at least some exemplary embodiments, the post used for the medical pendant box body can have the following features: by the innovative design of the post used for the medical pendant box body, the medical pendant box body can possess a standardised interface, without involving complicated (e.g., involved arrangement) connecting electrical cables, being easy for disassembly and assembly, and the position of a medical accessory being capable of being freely adjusted.

DETAILED DESCRIPTION AND INDUSTRIAL APPLICABILITY

The present invention is further described in connection with drawings and particular embodiments as follows and elaborated in more detail in the following description in order to illustrate the present invention, but it is evident that the present invention can be implemented in many other ways which are different from those described herein. The scope of the present invention should not be limited by the specific content of embodiments of the present invention herein.

Figure 1:
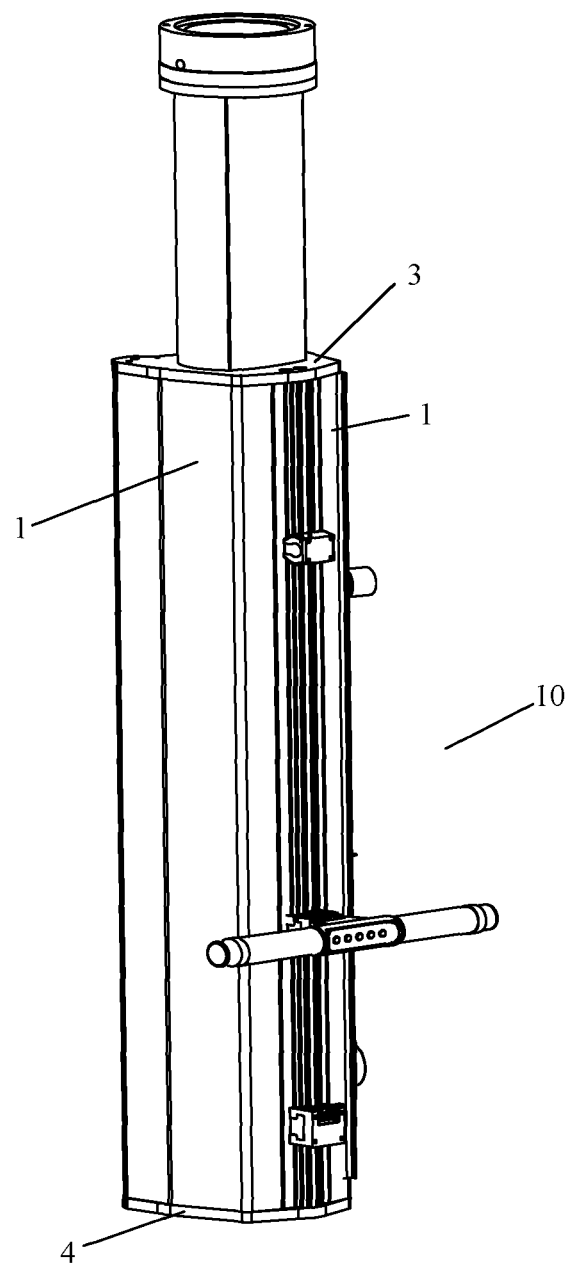
FIG. 1 illustrates a three-dimensional view for the medical pendant box body of an embodiment of the present invention.
Figure 2:
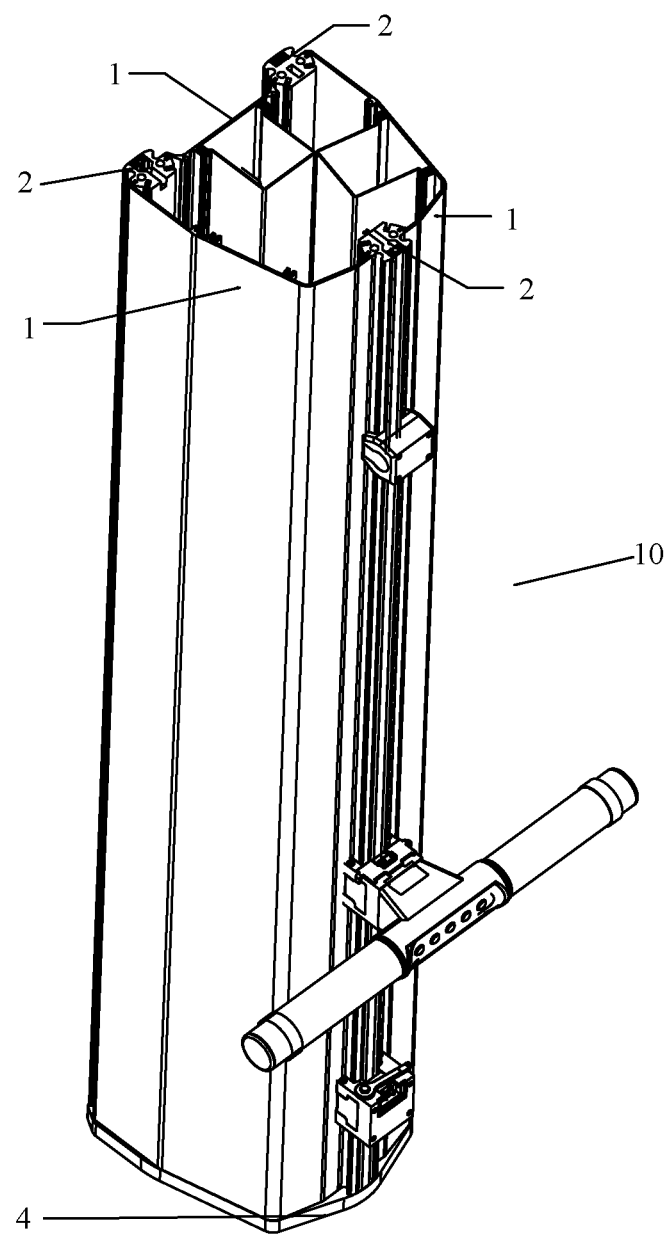
FIG. 2 illustrates a three-dimensional view for the medical pendant box body of an embodiment of the present invention, in which the upper base plate is removed for clarity.
Figure 3:
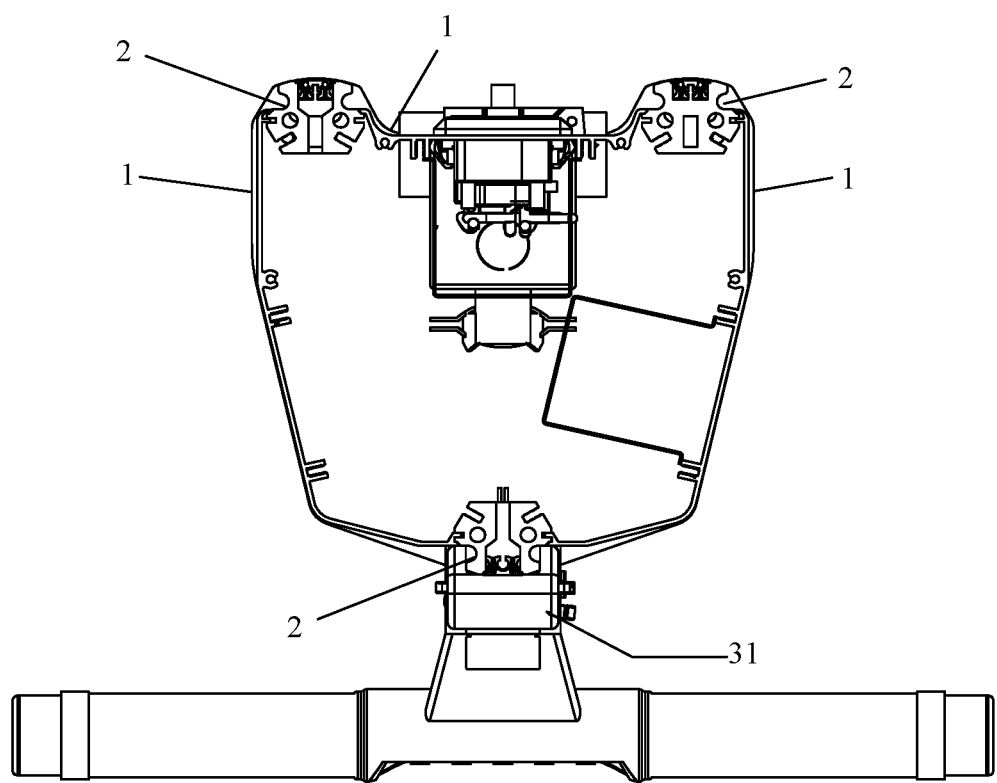
FIG. 3 illustrates the top view of the medical pendant box body shown in FIG. 2.
Figure 4:
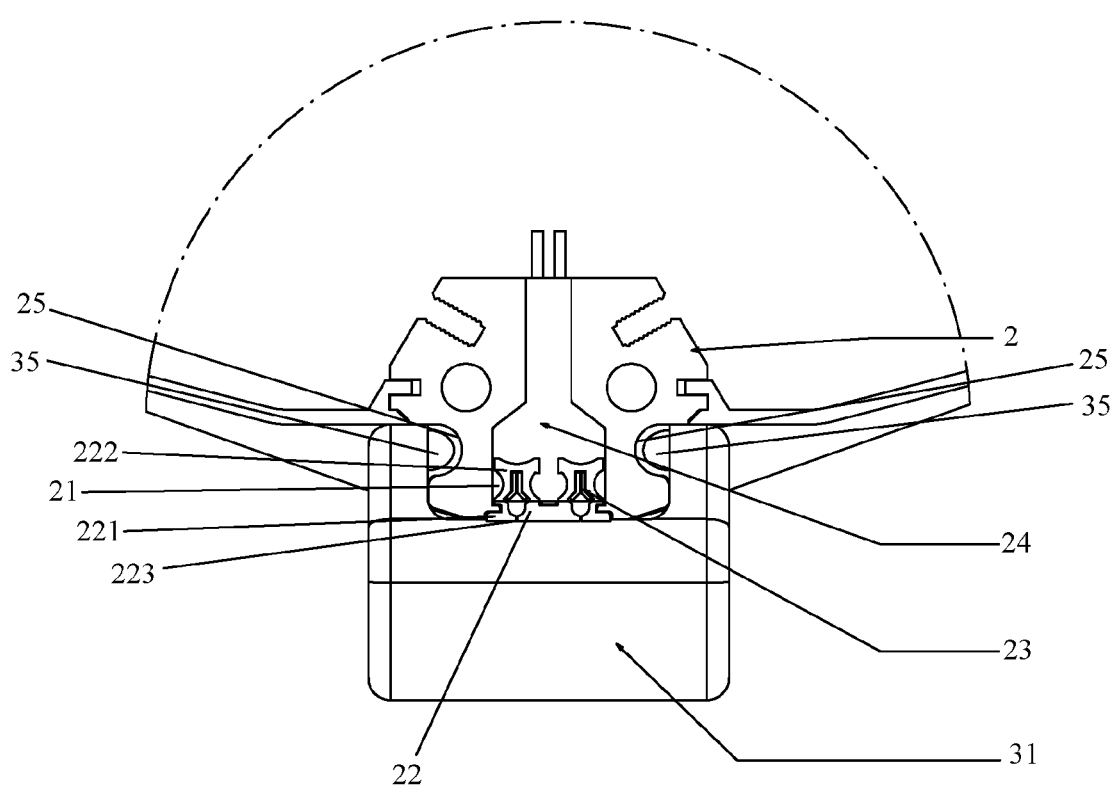
FIG. 4 illustrates a partial enlarged view of a portion of the lower part in FIG. 3, for example showing the electrical interface and the mechanical interface of the post in the medical pendant box body.

FIG. 1 and FIG. 2 respectively show the three-dimensional views for a medical pendant (e.g., the medical pendant box body 10 of an embodiment of the present invention), in which the upper base plate may be removed from the medical pendant box body 10 in FIG. 2 for clarity. FIG. 3 shows the top view of the medical pendant box body 10 shown in FIG. 2. FIG. 4 shows a partial enlarged view of a portion of the lower part in FIG. 3, for example showing the electrical interface and the mechanical interface of a medical pendant post (e.g., post 2) in the medical pendant box body 10.

The medical pendant box body 10 of the present invention may comprise at least two panels 1, at least two posts 2 extending along the longitudinal direction of the medical pendant box body, an upper base plate 3 and a lower base plate 4. The at least two panels 1 may be respectively fixed to the at least two posts 2, the upper base plate 3 and the lower base plate 4 may be fixed to the upper edge and the lower edge of each panel 1 of at least two panels 1, respectively.

Note that, "upper", "lower", "front", "rear", "left", "right" and the like used herein are exemplary directions defined to facilitate the description of the invention, as shown in FIG. 3, the direction toward the reader is "upper", the direction away from the reader is "lower", the direction of the bottom side in the paper is "front", the direction of the top side in the paper is "rear", the direction of the left side in the paper is "left", and the direction of the right side in the paper is "right". Of course, those skilled in the art on the basis of the present invention can understood that "upper", "lower", "front", "rear", "left", "right" and other directions are exemplary and can also be defined in other ways, which also fall into the protective scope of the present invention.

As shown in FIG. 4, at least one post 2 of the at least two posts may be provided with an electrical interface. The electrical interface may comprise a groove disposed in post 2 (e.g., an inner groove 21 located on the post 2) and extending along the longitudinal direction of the post (e.g., the groove extending along the longitudinal direction of the medical pendant post), an insulator disposed in the groove (e.g., insulator 22 accommodated within the inner groove 21), and a conductor disposed within the insulator (e.g., a conductor 23 substantially sealed within the insulator 22).

In this way in at least some exemplary embodiments, the medical pendant box body can possess a standardised electrical interface, without involving complicated connecting electrical cables, can have simplified disassembly and assembly, and the position of a medical accessory may be capable of being freely adjusted.

As shown in FIG. 4, at least one post 2 of the at least two posts may be provided with a mechanical interface, the mechanical interface comprising a concave curved portion 25 for matching to the convex curved portion 35 of the mechanical connecting piece 31.

In at least some exemplary embodiments, the medical pendant box body can possess a standardised mechanical interface, which may simplify disassembly and assembly, and the position of a medical accessory may be capable of being freely adjusted. Furthermore, via the same post in the medical pendant box body, both the mechanical connection and the electrical connection can be achieved, the number of the components needed may be reduced, and the connection reliability may be suitable.

Although the examples given above describe the circumstance with respect to the matching of the concave curved portion of the post to the convex curved portion of the mechanical connecting piece, a person skilled in the art would understand that the form of matching of the convex curved portion of the post to the concave curved portion of the mechanical connecting piece can also be used. Such variation may also fall into the protection scope of the present invention.

In at least some exemplary embodiments, as shown in FIGS. 1 and 2, posts 2 may extend along the longitudinal direction of the medical pendant box body 10 and may pass through (e.g., the entire) the length of the medical pendant box body 10. In this way, via a mechanical connecting piece, the location of the medical accessories can be steplessly adjusted along the longitudinal direction of the medical pendant box body.

In at least some exemplary embodiments, the inner groove 21 may extend across (e.g., the entire) the length of the post 2. For example, as shown in FIG. 4, the inner groove 21 may be located at the front surface of the post 2. In this way, it is easy for the extrusion molding of the post, effectively reducing the processing cost. For example, the number of the inner grooves 21 on the post 2 may be one groove. In this way, the simple and reliable electrical connection may be realized, meanwhile simplifying the structural design of the post and reducing the processing cost.

In at least some exemplary embodiments, the insulator 22 may extend along the longitudinal direction of the post. For example, the insulator 22 may also extend across the (e.g., entire) length of the post 2.

In at least some exemplary embodiments, the conductor 23 may extend along the longitudinal direction of the post. For example, the conductor 23 may also extend across the (e.g., entire) length of the post 2.

In at least some exemplary embodiments, the medical pendant box body can freely adjust the position of a medical accessory across the (e.g., entire) length of the post (or the entire length of the medical pendant box body), and may easily and quickly realize the electrical connection and/or the mechanical connection.

In at least some exemplary embodiments, as shown in FIG. 4, the inner groove 21 may be substantially filled when the insulator 22 is accommodated within the inner groove 21 and the conductor 23 is sealed within the insulator 22.

In at least some exemplary embodiments, the electrical interface may have good reliability and insulation performance, effectively preventing the infiltration of water or other cleaning agents during the cleaning process in a hospital.

In at least some exemplary embodiments, as shown in FIG. 4, the number of the insulators 22 within the inner groove 21 may be two, and one conductor 23 may be sealed within each insulator 22. For example, the insulator 22 may comprise an insulator front part 221 and an insulator rear part 222. For example, the insulator front parts 221 of the two insulators 22 can be formed integrally so as to substantially prevent the infiltration of water or other cleaning agents during the cleaning process in a hospital.

In at least some exemplary embodiments, as shown in FIG. 4, the cross section of the conductor 23 may be substantially Y-shaped. Also for example, the cross section of the conductor 23 can also be substantially Ω-shaped.

In at least some exemplary embodiments, via the appropriate settings of the shape and number of the above insulators and conductors, the simple and reliable connection between the plug of the electrical accessory and the conductor inside the post can be achieved.

In at least some exemplary embodiments, as shown in FIG. 4, in the case that the insulator 22 comprises an insulator front part 221 and an insulator rear part 222, the conductor 23 may be sealed within the insulator rear part 222, the insulator front part 221 may have a substantially flat front surface and a gap 223 extending along the longitudinal direction of the medical pendant box body.

In at least some exemplary embodiments, the insulator 22 (comprising an insulator front part 221 and/or an insulator rear part 222) may possess a predetermined elasticity. For example, the insulator front part 221 may possess a certain (e.g., predetermined) elasticity. Again, for example, the insulator rear part 222 may possess a certain (e.g., predetermined) elasticity. Again, for example, both the insulator front part 221 and the insulator rear part 222 may possess a certain (e.g., predetermined) elasticity.

In at least some exemplary embodiments, the width size (e.g., predetermined width size) of the gap 223 and the elasticity (e.g., predetermined elasticity) of the insulator front part 222 may be designed so that the gap 223 can be provided for inserting the plug of the electrical accessory and the insulator front part 221 may be substantially sealed before inserting the plug.

In at least some exemplary embodiments, the width size (e.g., predetermined width size) of the inner groove 21 and the elasticity (e.g., predetermined elasticity) of the insulator 22 may be designed to make the insulator 22 (e.g., insulator rear part 222) produce suitable predeformation so as to produce certain pre-pressure, so that when the plug of an electrical accessory is inserted into the electrical interface to connect to the conductor 23, the pre-pressure (e.g., predetermined pre-pressure) may substantially prevent the plug from disengaging from the conductor 23.

In at least some exemplary embodiments, as shown in FIG. 4, the conductor 23 may be connected to the control board of the medical pendant via a connector 24.

In at least some exemplary embodiments, the mechanical connecting piece 31 can be used for installing various medical accessories, for example, a control handle, an infusion pole, a display arm, and a medical guide rail.

The height of the medical accessories can be arbitrarily adjusted (e.g., adjusted to any suitable position) after the medical accessories are installed on the interfaces of the posts, and they can be interchanged on different posts.

The conductor 23 provided in post 2 can achieve multiple functions, for example, providing air brake control, electromagnetic brake control, and motor control which may be used for controlling the medical pendant; providing direct current supply, for example, an environment lamp can be directly installed on the conductor; realizing the simultaneous supply of the power and control signals; and supplying video or audio signals, such as the data of a pulsimeter, etc.

It will be apparent to those skilled in the art that various modifications and variations can be made to the disclosed method and apparatus. Other embodiments will be apparent to those skilled in the art from consideration of the specification and practice of the disclosed method and apparatus. It is intended that the specification and the disclosed examples be considered as exemplary only, with a true scope being indicated by the following claims.

What is claimed is:

1. A medical pendant, comprising:
   a medical pendant post that extends along a longitudinal direction of the medical pendant, the medical pendant post including an electric interface;
   wherein the electric interface includes
      a groove disposed in the medical pendant post and extending along a longitudinal direction of the medical pendant post,
      an insulator disposed in the groove, and
      a conductor disposed within the insulator;
   wherein a medical accessory is disposed on the medical pendant post; and
   wherein the conductor is completely surrounded by the insulator.

2. The medical pendant of claim 1, wherein the groove is substantially filled when the insulator is disposed in the groove and the conductor is disposed within the insulator.

3. The medical pendant of claim 1, wherein the conductor is substantially sealed within the insulator.

4. The medical pendant of claim 1, wherein a cross section of the conductor is substantially Y-shaped or substantially Ω-shaped.

5. The medical pendant of claim 1, wherein:
   the insulator includes an insulator front part and an insulator rear part;
   the conductor is substantially sealed within the insulator rear part; and
   the insulator front part has a substantially flat front surface and a gap extending along the longitudinal direction of the medical pendant.

6. The medical pendant of claim 5, wherein a predetermined width size of the gap and a predetermined elasticity of the insulator front part are configured to substantially seal the insulator front part when an electrical accessory plug is not plugged into the medical pendant post.

7. The medical pendant of claim 1, wherein:
   a predetermined width size of the groove and a predetermined elasticity of the insulator are configured to produce a predeformation producing a predetermined pre-pressure; and
   when a plug of an electrical accessory is inserted into the electrical interface to connect to the conductor, the pre-pressure substantially prevents the plug from disengaging from the conductor.

8. The medical pendant of claim 1, wherein the conductor is connected to a control board of the medical pendant via a connector.

9. The medical pendant of claim 1, wherein:
   the medical pendant post includes a mechanical interface; and
   the mechanical interface includes one of a concave curved portion and a convex curved portion for matching to one of the convex curved portion and the concave curved portion of a mechanical connecting piece.

10. The medical pendant of claim 9, wherein the mechanical connecting piece is used for installing a medical accessory.

11. A medical pendant, comprising:
    a medical pendant post that extends along a longitudinal direction of the medical pendant, the medical pendant post including an electric interface;
    wherein the electric interface includes
       a groove disposed in the medical pendant post and extending along a longitudinal direction of the medical pendant post,
       an insulator disposed in the groove, and
       a conductor that is completely surrounded by the insulator; and
    wherein the groove is substantially filled when the insulator is disposed in the groove and the conductor is completely surrounded by the insulator.

12. The medical pendant of claim 11, wherein a cross section of the conductor is substantially Y-shaped or substantially Ω-shaped.

13. The medical pendant of claim 11, wherein:
    the insulator includes an insulator front part and an insulator rear part;
    the conductor is substantially sealed within the insulator rear part; and
    the insulator front part has a substantially flat front surface and a gap extending along the longitudinal direction of the medical pendant.

14. The medical pendant of claim 13, wherein a predetermined width size of the gap and a predetermined elasticity of the insulator front part are configured to substantially seal the insulator front part when an electrical accessory plug is not plugged into the medical pendant post.

15. The medical pendant of claim 11, wherein:
    a predetermined width size of the groove and a predetermined elasticity of the insulator are configured to produce a predeformation producing a predetermined pre-pressure; and
    when a plug of an electrical accessory is inserted into the electrical interface to connect to the conductor, the pre-pressure substantially prevents the plug from disengaging from the conductor.

16. A medical pendant, comprising:
    a first panel and a second panel;
    a first medical pendant post attached to the first panel and a second medical pendant post attached to the second panel, the first and second medical pendant posts extending along a longitudinal direction of the medical pendant;
    an upper base plate attached to respective upper edges of the first and second panels and a lower base plate attached to respective lower edges of the first and second panels; and
    at least one of the first and second medical pendant posts including an electrical interface;
    wherein the electric interface includes
       a groove disposed in at least one of the first and second medical pendant posts and extending along a longitudinal direction of at least one of the first and second medical pendant posts,
       an insulator disposed in the groove, and
       a conductor disposed within the insulator; and
    wherein the conductor is completely surrounded by the insulator.

17. The medical pendant of claim 16, wherein the groove is substantially filled when the insulator is disposed in the groove and the conductor is disposed within the insulator.

18. The medical pendant of claim 16, wherein the conductor is substantially sealed within the insulator.

19. The medical pendant of claim 16, wherein a cross section of the conductor is substantially Y-shaped or substantially Ω-shaped.

20. The medical pendant of claim 16, wherein the conductor is connected to a control board of the medical pendant via a connector.

* * * * *